US008329992B2

(12) United States Patent
Busov et al.

(10) Patent No.: US 8,329,992 B2
(45) Date of Patent: Dec. 11, 2012

(54) MANIPULATION OF PLANTS BY TRANSFORMATION WITH SEQUENCES PROMOTING CELL DIVISION

(75) Inventors: Victor B. Busov, Houghton, MI (US); Steven H. Strauss, Corvallis, OR (US)

(73) Assignees: The State of Oregon Acting by and Through The State Board of Higher Education on Behalf of Oregon State University, Corvallis, OR (US); Michigan Technological University, Houghton, MI (US)

( * ) Notice: Subject to any disclaimer, the term of this patent is extended or adjusted under 35 U.S.C. 154(b) by 299 days.

(21) Appl. No.: 12/663,063

(22) PCT Filed: Jun. 9, 2008

(86) PCT No.: PCT/US2008/066293
§ 371 (c)(1),
(2), (4) Date: Dec. 4, 2009

(87) PCT Pub. No.: WO2008/154479
PCT Pub. Date: Dec. 18, 2008

(65) Prior Publication Data
US 2010/0175152 A1    Jul. 8, 2010

Related U.S. Application Data

(60) Provisional application No. 60/933,646, filed on Jun. 7, 2007.

(51) Int. Cl.
*C12N 15/82* (2006.01)
*C12N 15/29* (2006.01)
*C12N 5/10* (2006.01)
*C07K 14/00* (2006.01)

(52) U.S. Cl. ........ 800/290; 800/286; 800/303; 800/319; 435/320.1; 435/419; 435/468; 536/23.6; 530/350; 530/379

(58) Field of Classification Search ........................ None
See application file for complete search history.

(56) References Cited

U.S. PATENT DOCUMENTS

| | | | | |
|---|---|---|---|---|
| 6,395,892 | B1 * | 5/2002 | Strauss et al. | 536/24.1 |
| 6,696,623 | B1 * | 2/2004 | Doerner et al. | 800/298 |
| 7,196,245 | B2 * | 3/2007 | Jiang et al. | 800/278 |
| 2005/0198711 | A1 | 9/2005 | Evans | |
| 2006/0070142 | A1 | 3/2006 | Yanofsky | |

FOREIGN PATENT DOCUMENTS

WO    2011038332    3/2011

OTHER PUBLICATIONS

Jiang et al. 2007a. Alignment of sequence encoding SEQ ID No. 2 with SEQ ID No. 499 of US Patent 7,196,245.*
Jiang et al. 2007b. Alignment of SEQ ID No. 1 with SEQ ID No. 499 of US Patent 7,196,245.*
Altshul, S.F. et al., "Gapped BLAST and PSI-BLAST: a new generation of protein database search programs," Nucl. Acids Res. (1997) 25(17):3389-3402.
Bonke, M. et al., "APL regulates vascular tissue identitiy in *Arabidopsis*," Nature (2003) 426(6963):181-186.
Brunner et al., "Poplar genome sequence: functional genomics in an ecologically dominant plant species," Trends in Plant Science (2004) 9:49-56.
Byzova et al., "*Arabidopsis* sterile apetala, a multifunctional gene regulating influorescence, flower and ovule development," Genes & Development (1999) 13:1002-1014.
Chen, H. et al., "Enhanced recovery of transformants of *Agrobacterium tumefaciens* after freeze-thaw transformation and drug selection," Biotechniques (1994) 16:664-668.
Gleave, A., "A versatile binary vector system with a T-DNA organisational structure conducive to efficient integration of cloned DNA into the plant genome," Plant Mol. Biol. (1992) 20:1203-1207.
Han, K.H. et al., "An *Agrobacterium tumefaciens* transformation protocol effective on a variety of cottonwood hybrids (genus *Populus*)," Plant Cell Rep. (2000) 19:315-320.
Kumar, M. et al., "An update on the nomenclature for the cellulose synthase genes in *Populus*," Trends in Plant Sci. (2009) 14:248-254.
Liu, Y.G. et al. "Efficient isolation and mapping of *Arabidopsis thaliana* T-DNA insert junctions by thermal asymmetric interlaced PCR," Plant J. (1995) 8:457-463.
Matsumura, Y. et al., "Characterization of genes in the asymmetric leaves2/lateral organ boundaries (AS2/LOB) family in *Arabidopsis thaliana*, and functional and molecular comparisons between AS2 and other family members," Plant J. (2009) 58(3):525-537.
Shuai, B. et al., "The lateral organ boundaries gene defines a novel, plant-specific gene family," Plant Physiol. (2002) 129(2):747-761.
Sterky et al., "A *Populus* EST resource for plant functional genomics," Proc. Natl. Acad. Sci. USA (2004) 101:13951-13956.
Tan, G.H. et al., "SiteFinding-PCR: a simple and efficient PCR method for chromosome walking," Nucl. Acids Res. (2005) 33(13):e122.
Tuskan et al., "The genome of black cottonwood, *Populus trichocarpa* (Torr. & Gray)," Science (2006) 313:1596-1604.
UniProtKB/TrEMBL Direct Submission Accession B9HU24, Jun. 16, 2009, retrieved from internet (Nov. 12, 2010) http://www.uniprot.org/uniprot/B9HU24.txt?version=3>.
Wilkins, O. et al., "Expansion and diversification of the *Populus* R2R3-Myb family of transcription factors," Plant Physiol. (2009) 149(2):981-993.
Zhao, C. et al., "The xylem and phloem transcriptomes from secondary tissues of the *Arabidopsis* root-hypocotyl," Plant Physiol. (2005) 138(2):803-818.
Zhu, Q.H. et al., "DPTF: a database of poplar transcription factors," Bioinformatics (2007) 23(10):1307-1308.
International Search Report and Written Opinion for Application No. PCT/US2008/066293 dated Oct. 15, 2008 (6 pages).
International Search Report and Written Opinion for Application No. PCT/US10/050371 dated Feb. 2, 2011 (11 pages).
Invitation to Pay Additional Fees for Application No. PCT/US2010/050371 dated Nov. 23, 2010 (2 pages).

* cited by examiner

*Primary Examiner* — David T Fox
(74) *Attorney, Agent, or Firm* — Michael Best & Friedrich LLP (57) ABSTRACT

Polynucleotides encode polypeptides for increasing the rate of growth of plants. Introduction of the polynucleotides into plants produces plants having altered characteristics, such as increased growth, increased leaf area and reduced fertility. Expression of polypeptides in plants or plant cells promotes cell division. Expression of the polynucleotides in plants in the antisense orientation produces plants that are sterile or have smaller leaves.

24 Claims, 2 Drawing Sheets

SEQUENCE LISTING

<160> NUMBER OF SEQ ID NOS: 8

<210> SEQ ID NO 1
<211> LENGTH: 1380
<212> TYPE: DNA
<213> ORGANISM: Poplar hybrid

<400> SEQUENCE: 1

```
atgtcttcct cctcctcctc ctcatcatca tctagcagtg gcaatggcaa tggcagcggt      60
ggtggtaatt acggtgcaag aagagccggt gagtacgaag ggccatcaag gtctcgtcca     120
agagccatta acgaggtttg gcctgagcct tttctggaag ctcttgctgc ccaagtcgcc     180
attgatgctt ctcgccttgt cggccggctg gtcgcggcac aggcacttgc caatgtattt     240
caggtgtgtt caacgtggcg agcagtctcg cgttcggatc ctctttggca ccgtctcact     300
cgcggtatct ggggccgcac caaccttttc catgacactt ggcgagagga gtatatctac     360
cgccaccaaa cggcccaaaa cttccgatcc ggaagagctg tccatttcgc tctccacttt     420
gatccagctg atgtggatga ccccaacgac cctgatgctc taatatgccg ctgtctcgct     480
ttctccgatc gctaccttgc atgcggtttt gctgacggcg ctgtccgcct ctttgatctc     540
accacgcgcc ttcatgcacg cactttccgc cctgaacacc atgaccgcct gggcaggttc     600
tctcgtgcgg tctcgggcat cgtcatcacg gccacacgct tggtgtttgc cacgttagat     660
ggtgatatcc acgtggcggc ggtaaatagc aatgccaatc cacggagggc ccgcttaggt     720
gaggtgttga acgacgggc attagtggac ttcacgggcc gtgggcgatg gtgggtgggc     780
ctatacgctg ggcttccggg ccgggcctat cgtgtctggg atggtaacac cgaagaacct     840 ctcttgaag gcggggcgtt gactgaccca gaggctgtgt tgggttggca cacgttgaca     900
gaagtgactg agtttgtggg ccgagtcagg gtcacgagtc aggaatcggt cgtggcatgc     960
acgagttcga gacttgttat ttttgatttg ggggaccttg gggctgtact aagggaggag    1020
gactacacta acaggagagg catcttggtg ggttccttcg acgtatgcaa tgaggcgtat    1080
gtgattgtag atggcagggg gaatgctagc gtgcgcaggg cggacacctc ggaggagatg    1140 tgtggctta ccgtgaggcc tccaagggga gtgcttgggt gcatgaatgg tgggtacgtg    1200
ctaacgtgcg cgggtggtgt agtaagggta tggcagatag agcagcctgg tcgccaagag    1260
tatttgtata gcttcaggga gaggataggc gaggtaaacg ctctcgttgc agatgagagg    1320
cacgtggcag cagcatcaag tgacacgaat atacacctgt gggattttgg ggcacagtag    1380
```

<210> SEQ ID NO 2
<211> LENGTH: 459
<212> TYPE: PRT
<213> ORGANISM: Poplar hybrid

<400> SEQUENCE: 2

```
Met Ser Ser Ser Ser Ser Ser Ser Ser Ser Ser Ser Gly Asn Gly
 1               5                  10                  15
```

-continued

Asn Gly Ser Gly Gly Asn Tyr Gly Ala Arg Arg Ala Glu Tyr
                20              25              30

Glu Gly Pro Ser Arg Ser Arg Pro Arg Ala Ile Asn Glu Val Trp Pro
            35              40              45

Glu Pro Phe Leu Glu Ala Leu Ala Ala Gln Val Ala Ile Asp Ala Ser
 50              55              60

Arg Leu Val Gly Arg Leu Val Ala Ala Gln Ala Leu Ala Asn Val Phe
 65              70              75              80

Gln Val Cys Ser Thr Trp Arg Ala Val Ser Arg Ser Asp Pro Leu Trp
                85              90              95

His Arg Leu Thr Arg Gly Ile Trp Gly Arg Thr Asn Leu Phe His Asp
            100             105             110

Thr Trp Arg Glu Glu Tyr Ile Tyr Arg His Gln Thr Ala Gln Asn Phe
            115             120             125

Arg Ser Gly Arg Ala Val His Phe Ala Leu His Phe Asp Pro Ala Asp
    130             135             140

Val Asp Asp Pro Asn Asp Pro Asp Ala Leu Ile Cys Arg Cys Leu Ala
145             150             155             160

Phe Ser Asp Arg Tyr Leu Ala Cys Gly Phe Ala Asp Gly Ala Val Arg
                165             170             175

Leu Phe Asp Leu Thr Thr Arg Leu His Ala Arg Thr Phe Arg Pro Glu
            180             185             190

His His Asp Arg Leu Gly Arg Phe Ser Arg Ala Val Ser Gly Ile Val
    195             200             205

Ile Thr Ala Thr Arg Leu Val Phe Ala Thr Leu Asp Gly Asp Ile His
    210             215             220

Val Ala Ala Val Asn Ser Asn Ala Asn Pro Arg Arg Ala Arg Leu Gly
225             230             235             240

Glu Val Leu Asn Asp Gly Ala Leu Val Asp Phe Thr Gly Arg Gly Arg
                245             250             255

Trp Trp Val Gly Leu Tyr Ala Gly Leu Pro Gly Arg Ala Tyr Arg Val
            260             265             270

Trp Asp Gly Asn Thr Glu Glu Pro Leu Phe Glu Gly Gly Ala Leu Thr
            275             280             285

Asp Pro Glu Ala Val Leu Gly Trp His Thr Leu Thr Glu Val Thr Glu
    290             295             300

Phe Val Gly Arg Val Arg Val Thr Ser Gln Glu Ser Val Val Ala Cys
305             310             315             320

Thr Ser Ser Arg Leu Val Ile Phe Asp Leu Gly Asp Leu Gly Ala Val
                325             330             335

Leu Arg Glu Glu Asp Tyr Thr Asn Arg Arg Gly Ile Leu Val Gly Ser
            340             345             350

Phe Asp Val Cys Asn Glu Ala Tyr Val Ile Val Asp Gly Arg Gly Asn
            355             360             365

Ala Ser Val Arg Arg Ala Asp Thr Ser Glu Glu Met Cys Gly Phe Thr
    370             375             380

Val Arg Pro Pro Arg Gly Val Leu Gly Cys Met Asn Gly Gly Tyr Val
385             390             395             400

Leu Thr Cys Ala Gly Val Arg Val Trp Gln Ile Glu Gln Pro
                405             410             415

Gly Arg Gln Glu Tyr Leu Tyr Ser Phe Arg Glu Arg Ile Gly Glu Val
            420             425             430

Asn Ala Leu Val Ala Asp Glu Arg His Val Ala Ala Ala Ser Ser Asp

```
                435                 440                 445
Thr Asn Ile His Leu Trp Asp Phe Gly Ala Gln
    450                 455

<210> SEQ ID NO 3
<211> LENGTH: 2820
<212> TYPE: DNA
<213> ORGANISM: Poplar hybrid

<400> SEQUENCE: 3
tagtttatac acgtctttac agtacatgtt gtggatagat tttcctttga tattgtggtc    60
aatttgacac gaattctgta gcatttcttt cttttctcga gaggctgggg tgttcttgga   120
ggtttcccag ccctgcaaag acggcgggga gatatagtta ggttcagttt caggttcatg   180
tgagaaactg ctggttcttc tatttagcca aggtgtgctc aggtgctttt gtacacgtac   240
cactctttgg accaactttc ttttgtactc tcttgtccat ttccaagtga aactttatc    300 gacgagcttg ctttagtttt tattctttgt atagtcaagg attttcaaat atagtacatg   360
aacactaacg ggaaatacag aggtagctta gtaaatttt gtttctgcgg gggcacctcc    420
catcatcttt agttcactca cctgaacctg ctctcactac aagctcactg cgagctccct   480
gcatctacag tttcgctgag aaatcttacc acatcaacat tttaaagtga aaacgaaac    540 ctaaagaaaa cgaagaaaga aatcacgaca tcccacgaag aatcttaact agacaaatct   600 aaccatttt attttttttg aattgctaat gaaaattcca tctgatatgt cagcaatgtt    660
tatgaaaatg ctaatataat ttttttatca tatcatgctt tcgtccgaaa ttattggcag   720
aaattcttca tcatattttc tttcggtaaa tcaatgataa aatatttatc catgcttttg   780
gttaaaaatg tataaaaatg atgacaggaa gtcaaagcag cgaaggggaa tgagaataa    840 aaaatgttt ttcttagcgg ggaaacggat aacaatgacg acgaggccat ctttaaatat    900
agaattcaaa ttagaaattc ttaaagtttt tcctgcccgt ggctatgcgg acactaaagc   960
caaagaaata tcatcatcag tctttcccaa ccaattacca actaccaagc atgcatgacc  1020
attgactggg atcgaatgct atgagccttt ttatttattt atttatttgg tattgttatt  1080
ttcttaatta aaggcttatt aaaataatat ctttattatt tttaatatta tcacgttaaa  1140
attgtaagaa aaaacaggta aaaaacagtt aataaaatgc tttagcaggc actcatttca  1200
tcttttgtgc tggttaattc tctgggaacg tatgaggttc ggttcatcat ctgagcgttg  1260
atagtgataa gtgatagatt tacatggatt tggggagtga tttttttatta aaatattttt  1320 aagaaatgaa ttacaatgaa aaataaactg ggaattagat tctatatttg gttttgtaag  1380
gagaaatata tagaaaataa tatttttttat tctttaaaat attgaaaatt gaaaggtttt  1440
ttcccaagtt taaaggagga aaacactact ttcccctcgt aaaatgagtt gtatgctttt  1500
ctttgagttg aaaacacttc atgctactta tttttcaaat gggttatcaa ataattaatt  1560
tcttataaaa caaacgggtc tcttttttatt tttcatagag ttatcaaaga aaaaaaagat  1620
gcacgtaatt gtgaaggcta ctgtagagta tataacgtag agattttta ttttttatttt  1680 agttttgatg aaagaaacca tcttattgca gtgctcctac atatatggac atgtaattcc  1740
actgcctgtt aaaccaggca caagctgggt acttcgaggg tgcaggacac aacaaaaagc  1800
acttgaggtg gcatgaagaa atgaccaaat ccaaagcata tgatttgtga tgataaaaag  1860 gttgagttttt ctccaaaccg tgataaaaac tagaaaatca agcgtgaact tgctgtccct  1920
catgtctgtg ccccggtggc cacagcatat gatttgtgat gattattagc tatgtacaat  1980
ttgttctata gaatctatga aaaggtaact cgggcagtga attgcagtaa tgatttgcct  2040
```

```
gtgtggtggc caggcaagcc gatggagccc ttggaacgcg aggctcgtca cttcaaggta    2100
cttgcgagca caaccatggg ctcatcaaag tatcaaacta aaacagcaca gttcagagag    2160
agagagagag agggagagag agggagagag agagcagttc atacttcata gcattagcag    2220
cgcaatggaa ccaaactgcc gctaaaagga ttatcccaaa ttcgaacagt gcttgacctc    2280
gaggagcagc tccaccctgc cctcgctctt caaattgaag cttattttgc tgttcataag    2340
tacttagatc ttttttttaa ttttgtatga tctgtcaata tgagacatgc aacatcgacg    2400
cacctgggag aatgctggga aaataatgtg tgtgaatgta gagcaataca gtagtttaat    2460 tttttttataa atcaaaataa tatcattttg gttaaaaaaa tagtcaacaa tttataaccg    2520 agttttgac cgggtcttac caggccagat cagttggttc acctgagttt ttaattttc       2580 ttattttttg aaattcagct tggttccagt tccaaatcaa tcgggtctca agtcaatctg    2640
ttaaaccaga ttaaatttta aaattataat aatatgtaca acagattgaa tattttcatg    2700
agactctatc ttaaacatag atttaataat cttttagatt ttagatttta gatttgtttc    2760
tttattgtta tttggatacc gattccacca ttaaattata agtttataac acattaattg    2820

<210> SEQ ID NO 4
<211> LENGTH: 1806
<212> TYPE: DNA
<213> ORGANISM: Arabidopsis thaliana

<400> SEQUENCE: 4
gtttcctctc tcccccacca ttctttctcc tctctccgct tcttcttctt ccctgttcc      60 tcttataacc cctctcgtct catgtctacc tcctcctctt cttccgacaa cggagccggt    120
ggaagcggcg gcgttttcga ggccccatct ccatcccgcc ctcgccgcgg agccaacgat    180
gtttggccgg agcttttct tgaatctctc gccgttcaag ttgccgttaa cgcttccaca     240
tccgccggcc tcctcgccgc agctccggct cttgccaacg tttttcgggt ttgcaccacg    300
tggctagctg tctctcgctc cgaccatcta tggcaactac tatctcgcca gtttgggca    360 agaacacatt tgatgcacga cacgtggcgg gacgagttca tctaccgtca tcggacggct    420
agaaacttcc ggacgcgtac tcacacctac ttcactctcc aatttgaccc gtctgatgtg    480
gacgagcctg atagtctctc ttgccgttgt ctcaccctct cagacctcta cttagccgga    540
gggttcgccg acggaaccgt ccggcttttt cttctaaaca accgactcca cgtcaggacc    600
ttacggccac tctacgtgaa ccgctttggt agattctcac gagccgtctc aggcattgtt    660
atctccgact caaggctcac gttcgctacg atggacgag acatccacgt ggcggaaata     720
gacggtgttg gtcacacacg cacgcttac gcaggagata tagttaacga cggtgcgttg     780
gtagatttca ctggctgtgg acgttggtgg gtcggtcttt tcgcgggtgt gccaggtcgt    840
gcctttcaca tatgggactg taacagcgaa gagacaacat tcgtcggtgg tacactcacc    900 gacccctgaag ctgtcatggg atggcacacg ttaacagagc taacaacgtc ccttggccgt    960
ctcagaatct ccggtaacga gacgcggta gcatgcacga gatggagaat catggtgatc   1020
gatctaagaa accaaggagt gatcatcgga gaagacgaag agccacgtag aggactaata   1080
gtgacaggct tcgatgccaa cgacgaagcg tacgttagat tggacagtag aggaaacgct   1140
agcgtgcgaa gggtgaacac gcaacaaacg gtgtgtgagt tccgtgttag tggagcggcg    1200
cagagaagag taatgggttg tgttaataga ctgcacgcgc taatgtgcgc aggtggtata   1260
atgcgcgtgt gggaggtaga gagggagag tatctgtaca gtattaggga gagagtagga    1320
gaagttgacg ccattgttgc cgatgataga catgtggcgg ttgcgtcagc ttcatcaacg   1380
```

```
gctcagagta ttatacatct atgggatttc ggtgcactgt agcgtaccag attactaaaa    1440
tttttttttt taacttgaaa aaaaagaaac tattttctc tgaaaagcg aaaccctaaa      1500 cctaggtgta tatgtagggt ttctgattat aaattaaatt gggaaagtga cggagggaag    1560
atggtgacag gagggtgaaa tttacaaggg aaattgattc tttctacaaa gtttgaccaa    1620
aaaattaagt tactgttttt gtctaaaacc aaacaaagtg acttttct tgttgttctt      1680 gttttttcc ttgtgtttag ggctctctca attttgactt tgtacgaaat gtctttttt     1740 ttttcttcta cttgtaactc ttcactttac tggagtttat tattttgtat aatggtccca    1800
aaaaaa                                                                1806
```

<210> SEQ ID NO 5
<211> LENGTH: 446
<212> TYPE: PRT
<213> ORGANISM: Arabidopsis thaliana

<400> SEQUENCE: 5

```
Met Ser Thr Ser Ser Ser Ser Asp Asn Gly Ala Gly Gly Ser Gly
1               5                   10                  15

Gly Val Phe Glu Ala Pro Ser Pro Ser Arg Pro Arg Arg Gly Ala Asn
            20                  25                  30

Asp Val Trp Pro Glu Pro Phe Leu Glu Ser Leu Ala Val Gln Val Ala
        35                  40                  45

Val Asn Ala Ser Thr Ser Ala Gly Leu Leu Ala Ala Pro Ala Leu
    50                  55                  60

Ala Asn Val Phe Arg Val Cys Thr Thr Trp Leu Ala Val Ser Arg Ser
65                  70                  75                  80

Asp His Leu Trp Gln Leu Leu Ser Arg Gln Val Trp Ala Arg Thr His
                85                  90                  95

Leu Met His Asp Thr Trp Arg Asp Glu Phe Ile Tyr Arg His Arg Thr
            100                 105                 110

Ala Arg Asn Phe Arg Thr Arg His Thr Tyr Phe Thr Leu Gln Phe
        115                 120                 125

Asp Pro Ser Asp Val Asp Glu Pro Asp Ser Leu Ser Cys Arg Cys Leu
    130                 135                 140

Thr Leu Ser Asp Leu Tyr Leu Ala Gly Gly Phe Ala Asp Gly Thr Val
145                 150                 155                 160

Arg Leu Phe Leu Leu Asn Asn Arg Leu His Val Arg Thr Leu Arg Pro
                165                 170                 175

Pro Leu Arg Asp Arg Phe Gly Arg Phe Ser Arg Ala Val Ser Gly Ile
            180                 185                 190

Val Ile Ser Asp Ser Arg Leu Thr Phe Ala Thr Met Asp Gly Asp Ile
        195                 200                 205

His Val Ala Glu Ile Asp Gly Val Gly His Thr Arg Thr Ala Tyr Ala
    210                 215                 220

Gly Asp Ile Val Asn Asp Gly Ala Leu Val Asp Phe Thr Gly Cys Gly
225                 230                 235                 240

Arg Trp Trp Val Gly Leu Phe Ala Gly Val Pro Gly Arg Ala Phe His
                245                 250                 255

Ile Trp Asp Cys Asn Ser Glu Gly Thr Thr Phe Val Gly Gly Thr Leu
            260                 265                 270

Thr Asp Pro Glu Ala Val Met Gly Trp His Thr Leu Thr Glu Leu Thr
        275                 280                 285

Thr Ser Leu Gly Arg Leu Arg Ile Ser Gly Asn Glu Thr Ala Val Ala
```

```
                  290                 295                 300
Cys Thr Arg Trp Arg Ile Met Val Ile Asp Leu Arg Asn Gln Gly Val
305                 310                 315                 320

Ile Ile Gly Glu Asp Glu Glu Pro Arg Arg Gly Leu Ile Val Thr Gly
                325                 330                 335

Phe Asp Ala Asn Asp Glu Ala Tyr Val Arg Leu Asp Ser Arg Gly Asn
                340                 345                 350

Ala Ser Val Arg Arg Val Asn Thr Gln Gln Thr Val Cys Glu Phe Arg
            355                 360                 365

Val Ser Gly Ala Ala Gln Arg Arg Val Met Gly Cys Val Asn Arg Leu
370                 375                 380

His Ala Leu Met Cys Ala Gly Gly Ile Met Arg Val Trp Glu Val Glu
385                 390                 395                 400

Arg Gly Glu Tyr Leu Tyr Ser Ile Arg Glu Arg Val Gly Glu Val Asp
                405                 410                 415

Ala Ile Val Ala Asp Asp Arg His Val Ala Val Ala Ser Ala Ser Ser
                420                 425                 430

Thr Ala Gln Ser Ile Ile His Leu Trp Asp Phe Gly Ala Leu
            435                 440                 445

<210> SEQ ID NO 6
<211> LENGTH: 1368
<212> TYPE: DNA
<213> ORGANISM: Vitis vinifera

<400> SEQUENCE: 6
atgtcgtcgt cttcttcttc ttcctcctcg tcttcttcat cttcacaaga tggcgaggtt        60
ggtggtggag gtggtggggg tggtgatttc gagggtcctt cctcttctcg gcgacgttcc       120
ggaaatgggg tttggccgga gccttttgtg gaggctctgg cttcccaagt ggccattgat       180
gcttctcgga gcattggtcg tctggccgct gctcctgccc tcgccaatgt cttccaggtg       240
tgctcaacat ggcgggcagt gtctcgatcg gaccttctat ggcgcaacct ctgccgccgt       300
atctggggcc gggcacggcg gcttcatgac acatggcggg aagagtttat ctaccgccac       360
cgcaccgcca tgaactttcg gaaccgccgg tataactata cgacactgga ttttgaccca       420
gcttacgtca gctccggcac agccacagct ctctcctgcc gctgcctggc actctccgac       480
ttccacctcg ccgtgggttt cgaggatggc accgttcgcc tctttgacct cgccacccgc       540
ctccacgtca gcacctgcct ccctcatcac aatgttctta tgggtccctt ctcccgcgcc       600
gtctctggca tcatcctctc tcgcgcccgc ctcgtcttcg cttccctcca cggcgacgtc       660
aacgtcgcgg ctctcgacat cgttgccccct ctcgatcccg ttatccccac tcgccacggc       720
gccagcgacg gagccctagt cgacttcgcc ggctgcagcc gctggtgggt cggcctctac       780
gccggcgccc ctggccaagc cttccgcatc tgggatggcg aaaccgaaga gctcgtcttc       840
gtcggtggga ccctcaccga cccagaagcc gtcatgggct ggcacatgtt cacagagtta       900
gccgatttcg ttggccgagt gcgagtcacg agccaggaat cggccgtggc atgcacgagt       960
cgccgagtca tcgtcttcaa ccttagaaac ggaggcaatg tacacgggga caagagttc      1020 gcgccagggt ttatcgtggg cagcctcgac gccaacaatg aggcgtacgt tatcgtggac      1080
gggaggggcg tggctagcgt acgcaggcg gagaatctag aagaggtgtg caggtttgta      1140 gtggaggta cctcgcagag gcgagttttg gggtgcatga acgggggta cgccctgatg      1200 tgcatcggga gtgtgataag agcgtgggag gtggaacgtg gggtgtatct gtacaacttg      1260
agggaaagaa cgttagggga tctggttgcc atggtggcag atgatagata cgtggcagca      1320
```

```
tgcaacagtg acaccacgat tcacttgtgg gactttgggg cccaataa          1368
```

<210> SEQ ID NO 7
<211> LENGTH: 455
<212> TYPE: PRT
<213> ORGANISM: Vitis vinifera

<400> SEQUENCE: 7

```
Met Ser Ser Ser Ser Ser Ser Ser Ser Ser Ser Ser Gln
1               5                   10                  15

Asp Gly Glu Val Gly Gly Gly Gly Gly Gly Asp Phe Glu Gly
            20                  25                  30

Pro Ser Ser Arg Arg Ser Gly Asn Gly Val Trp Pro Glu Pro
        35                  40                  45

Phe Val Glu Ala Leu Ala Ser Gln Val Ala Ile Asp Ala Ser Arg Ser
    50                  55                  60

Ile Gly Arg Leu Ala Ala Pro Ala Leu Ala Asn Val Phe Gln Val
65              70                  75                  80

Cys Ser Thr Trp Arg Ala Val Ser Arg Ser Asp Leu Leu Trp Arg Asn
                85                  90                  95

Leu Cys Arg Arg Ile Trp Gly Arg Ala Arg Arg Leu His Asp Thr Trp
            100                 105                 110

Arg Glu Glu Phe Ile Tyr Arg His Arg Thr Ala Met Asn Phe Arg Asn
            115                 120                 125

Arg Arg Tyr Asn Tyr Thr Thr Leu Asp Phe Asp Pro Ala Tyr Val Ser
        130                 135                 140

Ser Gly Thr Ala Thr Ala Leu Ser Cys Arg Cys Leu Ala Leu Ser Asp
145                 150                 155                 160

Phe His Leu Ala Val Gly Phe Glu Asp Gly Thr Val Arg Leu Phe Asp
                165                 170                 175

Leu Ala Thr Arg Leu His Val Ser Thr Cys Leu Pro His Asn Val
            180                 185                 190

Leu Met Gly Pro Phe Ser Arg Ala Val Ser Gly Ile Ile Leu Ser Arg
            195                 200                 205

Ala Arg Leu Val Phe Ala Ser Leu His Gly Asp Val Asn Val Ala Ala
        210                 215                 220

Leu Asp Ile Val Ala Pro Leu Asp Pro Val Ile Pro Thr Arg His Gly
225                 230                 235                 240

Ala Ser Asp Gly Ala Leu Val Asp Phe Ala Gly Cys Ser Arg Trp Trp
                245                 250                 255

Val Gly Leu Tyr Ala Gly Ala Pro Gly Gln Ala Phe Arg Ile Trp Asp
            260                 265                 270

Gly Glu Thr Glu Leu Val Phe Val Gly Gly Thr Leu Thr Asp Pro
        275                 280                 285

Glu Ala Val Met Gly Trp His Met Phe Thr Glu Leu Ala Asp Phe Val
290                 295                 300

Gly Arg Val Arg Val Thr Ser Gln Glu Ser Ala Val Ala Cys Thr Ser
305                 310                 315                 320

Arg Arg Val Ile Val Phe Asn Leu Arg Asn Gly Gly Asn Val His Gly
                325                 330                 335

Glu Gln Glu Phe Ala Pro Gly Phe Ile Val Gly Ser Leu Asp Ala Asn
            340                 345                 350

Asn Glu Ala Tyr Val Ile Val Asp Gly Arg Gly Val Ala Ser Val Arg
        355                 360                 365
```

```
Arg Ala Glu Asn Leu Glu Glu Val Cys Arg Phe Val Val Gly Gly Thr
    370                 375                 380

Ser Gln Arg Arg Val Leu Gly Cys Met Asn Gly Tyr Ala Leu Met
385                 390                 395                 400

Cys Ile Gly Ser Val Ile Arg Ala Trp Glu Val Glu Arg Gly Val Tyr
                405                 410                 415

Leu Tyr Asn Leu Arg Glu Arg Thr Leu Gly Asp Leu Val Ala Met Val
                420                 425                 430

Ala Asp Asp Arg Tyr Val Ala Ala Cys Asn Ser Asp Thr Thr Ile His
                435                 440                 445

Leu Trp Asp Phe Gly Ala Gln
    450                 455

<210> SEQ ID NO 8
<211> LENGTH: 5197
<212> TYPE: DNA
<213> ORGANISM: Poplar hybrid

<400> SEQUENCE: 8
acatgtatag cgtatcaata tacgcgtata tacatggaaa gactctaaat cgcaaatata      60
tatagagaga gagaggtgga ggagtctccc ttgggaccct cacattgcgt ctttatctag     120 accttttttgt ccttgtttct ttgtagccca tattttcctt tttttcatag cttcgctcct    180
tatatattgt ttattaatta atgtcttcct cctcctcctc ctcatcatca tctagcagtg     240
gcaatggcaa tggcagcggt ggtggtaatt acggtgcaag aagagccggt gagtacgaag     300
ggccatcaag gtctcgtcca agagccatta acgaggtttg gcctgagcct tttctggaag     360
ctcttgctgc ccaagtcgcc attgatgctt ctcgccttgt cggccggctg gtcgcggcac     420
aggcacttgc caatgtattt caggtaaatg tattctcttg agactcacga tggttttaat     480
cttactctgt gtatgcataa gaagtggagg ccattttgtc tgtcgcatca atgggtttgt     540
cttgttgaga tgtgttagct gttttgagag gtaattatgc taatcagtta gcagccgggt     600
aggctgagag gtaggcgcaa tagaatagag tcacttatca ccatccggtg gatatggtac     660
cgaaaatgga caaaaacttg gtctagtcaa agcactgttt ggaatctgtc agggagctaa     720
aatgatgtta tgaactccat tggttttgta tacaaatata gattctgaga ctcttctgtt     780
tttatttcaa tggaaactga agaaatgctg acacagggta acagcagctt gggttggatg     840
tatacaagca tccaaggaga aaccatacct ttggaaggaa ctgcttttta atgggtccat     900
ttctaactaa atttatgtcc cttttggatg tagcagtttc atcttggcaa ttttttagttg    960 cttcatcttt tgaatgctcc taaagaaaat atccattttt ggaccccgtt tcatatcttg    1020
cggaaaagga ctcttttggt tttgaatttc tctttccctt tcctggcatg atttttatttt   1080 agctctataa tcccttgcct ttttgactca actttcttac cttgctaaaa gatccattga    1140
aataactttt ctaatgctaa aatgtggata gagacgtttg aaacctactt ttaactcggc    1200
taatactttt agacttctgc ccagattcaa tttttcggga gcaacatttt cttttttgctg   1260 tggaaacaac catctccgct tggtttttag gtaaagccaa atttgggga ttgacttgtt    1320 tatgacagtg aatcgaacat tctagggttt tgttcaaact gaatttctca atcaaacaaa   1380
accaaaatct tggtgatttt atacgaggag cagcagtctc cattaatagc aaagagcttt   1440
gagaaagttc tcatcattac atggtccaat gtagctcggg gatgggctga tttagatgga    1500
taggagctat gaagtgattg ttttactatt tttatatcaa acaatttagg cttctgtttt    1560
ggcaattaag aaggatatct cacaaaattga ccagtcttgt gggatcagtc aatagtcagc   1620
```

```
atgtgcaacg ccaaaagtac atggagccca tgctggtgc  ctggtttcat aaattgatgt    1680
cacttcagag atagggtctt ctcttcgctc aagccagagg cagtcagtcg gtgactcaac    1740
ttttattcct tgttatatcc tgtgttttta ctacctccat tttcatttct atcactgtct    1800
tctttcgttc ctctagtttt agcacagtaa atttcgtatc tcctcgttgg attctgaacc    1860
tttcatgaaa aacacttgtt caatggcttt agctttgtgt aactttcaag tcctggagac    1920
ctcgagggat tgttctagtg agtaaccaaa tctcttgtaa aatgtatatg atccaaactc    1980
aaacgggctt ttgtaaagct tgtacctagg aaagattcta atttatagat ctactatcat    2040
aactgccaat aacttggcag taagaatggt caaagaatta attaattatt atcaaaactg    2100
gaaggagtaa attatttaaa tcttaaaaaa acaagggagg aagttagaat tcattgattg    2160 aaagggggggg gggggatatg atgtagggta tgtgggaagt agaagttagg gggacaatcg    2220
aagaaaaagg tagtcggaga agatatggat tcgcttcttt taacgagaca agcctttggc    2280
caactctttc ttggtaatga gagagagaga gagagagaga gagagagatg ggaaagcacg    2340
cttcgagtta taatccttttt taacagtaaa tctaactcca tcttttatcc ttgtaataaa    2400
aatctcattc tgacacacac aacacatgtg tgtgtgtgtc gtgtgtgtgt gtctcttggc    2460
atgcggtggc ctttcttctt cttattttga attatgtctt gaaacctccc atgtttgatt    2520
catttctgta tagcgtttgt ggtggtgtaa actctctgct agcgtctgtc cttcagtgtt    2580
ctcaaagtaa tttccctccc tgctcaacca caactaatgg ttctttgacc cgaagatttt    2640
gtctctccct gcccgattgc atttagattt cgccattgta ctttgctgta ccttatcctg    2700
tatggcatag aggatgaatg aataagagta attataataa aaagttaaag tttataataa    2760
caataaagag agagagggt cgcttttctcc tgatagtagt aggatactgt tgatgtggtt    2820
taccacagca tgtctaggct agaagacaag tctgttctgc tttgaaaaga aacactttat    2880
gtgagagctc tgactggttc tgacgcatgg aacccattaa aataacatgt ctttctcttt    2940
tctctaacca ccctctacta cagctctcta gtccctagtc tctcttgcct gctatttcct    3000
gtctggcatc ggcatgtatg aattgggcac cagcttcaag ccttctcaca attaaaagct    3060
taaatgcgca tgcttttcaag tgcctcggca tactgacgtt tcccacact ctatgtgatc    3120 agcatttgta gatgacactg acacgttttg ctggatcggt tcttggagtt gttaatcat    3180 ttaaaatgcc ggcctcttta gcttggttgg tggtctttgt ttttttcacaa tattattatt    3240 attattaaga tgacccatgc attgatatat atatatatat atatatatat atatatatat    3300
atatatatat atatatatat atatatatat atgttatgaa acccatttaa attatggttt    3360
tttaagacat taattattaa tcaattttgt gaggtcacgt ctttcatcat caccttcttg    3420
tttttgttgc atccatggtg atcttcgtat tcttgcctta gctggtgcct ggtccattat    3480
ataatggcat cccatagtta tgtaaattta cttttcatgt ggagtagttt aaaaataaaa    3540
atcaatggcg tctcatagat ctccatctat gaacattaat tagttttctt ctactgtggt    3600
tccgtataat ccctacccac cagctaacga agccttaaac atggtgcttc tgctgaatca    3660
ctgaaccgta actagcaact tgctctagct agcttcgcat aagttcaaat gatggaataa    3720
aaaaaaatta tggctgaaag tttcattaca tgtatcttct gctagctgtt gttgcatgat    3780
gcaattgcta cgtgtgcatg catagccgtc gtctctgtat ttatcttttt atgctttaca    3840
tggtgtccac tttgtttcag gtgtgttcaa cgtggcgagc agtctcgcgt tcggatcctc    3900
tttggcaccg tctcactcgc ggtatctggg gccgcaccaa ccttttccat gacacttggc    3960
gagaggagta tatctaccgc caccaaacgg cccaaaactt ccgatccgga agagctgtcc    4020
```

```
atttcgctct ccactttgat ccagctgatg tggatgaccc caacgaccct gatgctctaa    4080
tatgccgctg tctcgctttc tccgatcgct accttgcatg cggttttgct gacggcgctg    4140
tccgcctctt tgatctcacc acgcgccttc atgcacgcac tttccgccct gaacaccatg    4200
accgcctggg caggttctct cgtgcggtct cgggcatcgt catcacggcc acacgcttgg    4260
tgtttgccac gttagatggt gatatccacg tggcggcggt aaatagcaat gccaatccac    4320
ggagggcccg cttaggtgag gtgttgaacg acggggcatt agtggacttc acgggccgtg    4380
ggcgatggtg ggtgggccta tacgctgggc ttccgggccg ggcctatcgt gtctgggatg    4440
gtaacaccga agaacctctc tttgaaggcg gggcgttgac tgacccagag gctgtgttgg    4500
gttggcacac gttgacagaa gtgactgagt ttgtgggccg agtcagggtc acgagtcagg    4560
aatcggtcgt ggcatgcacg agttcgagac ttgttatttt tgatttgggg gaccttgggg    4620
ctgtactaag ggaggaggac tacactaaca ggagaggcat cttggtgggt tccttcgacg    4680
tatgcaatga ggcgtatgtg attgtagatg gcagggggaa tgctagcgtg cgcagggcgg    4740
acacctcgga ggagatgtgt ggctttaccg tgaggcctcc aaggggagtg cttgggtgca    4800
tgaatggtgg gtacgtgcta acgtgcgcgg gtggtgtagt aagggtatgg cagatagagc    4860
agcctggtcg ccaagagtat ttgtatagct tcagggagag gataggcgag gtaaacgctc    4920
tcgttgcaga tgagaggcac gtggcagcag catcaagtga cacgaatata cacctgtggg    4980
attttggggc acagtaggtg gagggcacgg ggggtggggg tagggttagg gttaggcgac    5040
ctgacctaga aagggaaata gacctaagct aagatggagg ggggatggtg acaagagggg    5100
atgtaggctc tcggtagggt ttagatttag ttttagcacg aggaacctga tatctttgac    5160
ttgtatgaaa gtagcttgtg attttttgata tggagag                            5197
```

MANIPULATION OF PLANTS BY TRANSFORMATION WITH SEQUENCES PROMOTING CELL DIVISION

CROSS-REFERENCE TO RELATED APPLICATIONS

This application is a national stage filing under 35 U.S.C. 371 of International Application No. PCT/US2008/066293, filed on Jun. 9, 2008, which claims the benefit of priority to U.S. provisional application 60/933,646, filed on Jun. 7, 2007, which is are incorporated herein by reference in their entireties.

STATEMENT REGARDING FEDERALLY SPONSORED RESEARCH OR DEVELOPMENT

This invention was made with United States government support awarded by the following agencies:
CREES/USDA, Grant No. 2004-35300-14687
The United States government has certain rights in this invention.

INTRODUCTION

Modified plants having altered characteristics such as increased leaf size may increase the supply of leafy vegetables for food consumption, plant-derived pharmaceutical or industrial products, biomass supply for the generation of biofuels or contribute to carbon remediation programs. Increasing the leaf size of a plant may increase the overall photosynthetic capacity of the plant, which may result in an increased yield of plant material in leaves and other tissues.

SUMMARY

The invention provides an isolated polynucletide comprising a contiguous coding sequence encoding a polypeptide having at least 95% identity with SEQ ID NO: 2, and plants and plant cells containing such polynucleotides. In one aspect, the plant containing the isolated polynucleotide exhibits increased expression of the polypeptide, relative to a control plant, and may exhibit increased growth and/or reduced fertility.

In another aspect, the invention provides an isolated polypeptide comprising a sequence having at least 95% identity with SEQ ID NO: 2.

In another aspect, the invention provides methods of producing transgenic plants by introducing into a plant cell a polynucleotide encoding a polypeptide comprising an amino acid sequence having at least 95% identity with SEQ ID. NO 2, and regenerating the transformed cell to produce a transgenic plant. In one aspect, the transformed plant exhibits increased growth and/or reduced fertility.

In another aspect, the invention provides methods of producing transgenic plants by introducing into a plant cell a polynucleotide encoding a polypeptide comprising an amino acid sequence having at least 95% identity with the reverse complement (antisense) of SEQ ID. NO: 1 and regenerating the transformed cell to produce a transgenic plant. The polynucleotide is suitably operably linked to a promoter. In one aspect, the plant containing the antisense sequence exhibits decreased growth and/or sterility.

DETAILED DESCRIPTION

The present invention relates to novel polynucleotides and polypeptides and use of the polynucleotides and polypeptides for modifying the phenotype of plants or plant cells. The invention further provides modified plants or plant cells comprising the polynucleotides of the invention. Suitably, the modified plants or plant cells exhibit increased growth or cell division compared with control plants or plant cells. The polynucleotides and polypeptides are of the present invention are termed SAP polynucleotides and SAP polypeptides because they show some similarity to STERILE APETALA (SAP) sequences from *Arabidopsis thaliana*.

It was surprisingly discovered that increasing the expression of a SAP polypeptide in plants (for example, by introducing SEQ ID NO: 2 into the plant) results in plants that exhibit increased growth, larger leaves, and/or show reduced fertility or are sterile, relative to plants in which expression of the SAP polypeptide has not been increased.

SAP polynucleotides useful in the invention include SEQ ID NO: 1, which is derived from the hybrid poplar clone resulting from a cross of *Populus alba* and *Populus tremula*. One of skill in the art will appreciate that, given the degeneracy of the genetic code, many other suitable polynucleotides are encompassed within the invention. SEQ ID NO. 1 encodes the polypeptide shown in SEQ ID NO: 2. SEQ ID NO: 2 has 58% amino acid identity to the SAP polypeptide sequence from *Arabidopsis thaliana* (SEQ ID NO: 5). The cDNA for the SAP polypeptide from *Arabidopsis thaliana* is shown in SEQ ID NO: 4, from position 82 to position 1422 (including the stop codon). SEQ ID NO: 2 has 61% amino acid identity to a polypeptide sequence from *Vitis vinifera* (SEQ ID NO: 7). The polynucleotide encoding SEQ ID NO. 7 from *Vitis vinifera* is shown in SEQ ID NO: 6. The genomic structure of the polynucleotide containing the SAP polynucleotide coding sequence from *Poplar* hybrid (SEQ ID NO: 1) is shown in SEQ ID NO. 8. Position 1 of SEQ ID NO: 8 corresponds to position 9250675 of the sequenced genome and position 5197 of SEQ ID NO: 8 at corresponds to position 9245479 of the sequenced genome. SEQ ID NO: 8 contains the 5' UTR from position 1 to position 200, exon 1 from position 201 to position 443, an intron from position 444 to position 3860, exon 2 from position 3861 to position 4997 including the stop codon (to position 4994 excluding the stop codon), and the 3' UTR from position 4998 to position 5197.

Other suitable SAP polynucleotides of the invention encode a polypeptide comprising a sequence having at least about 80%, at least about 85%, at least about 90%, at least about 95%, at least about 98%, or at least about 99% identity with SEQ ID NO: 2, and include SEQ ID NO. 1. Percent identity may be determined using the algorithm of Altschul et al., *Nucleic Acids Res.* 25:3389-3402 (1997). Such algorithm is incorporated into the BLASTP program, which may be used to obtain amino acid sequences homologous to a reference polypeptide, as is known in the art. Suitably, the polynucleotide is an isolated polynucleotide, a recombinant polynucleotide or a synthetic polynucleotide and encodes SEQ ID NO. 2, and/or is a contiguous coding sequence encoding a polynucleotide having at least about 80%, at least about 85%, at least about 90%, at least about 95%, at least about 98%, or at least about 99% identity to SEQ ID NO: 2. As used herein, "contiguous" with respect to a coding sequence means that the nucleotides of the coding sequence are connected in an unbroken sequence.

Polynucleotides of the invention may be isolated or recombinant and may comprise a contiguous coding sequence encoding a polypeptide corresponding to the sequence from position 1 to position 81 of SEQ ID NO. 2 and/or from position 82 to position 459 of SEQ ID NO. 2, which are encoded by exon 1 and exon 2 of SEQ ID NO. 1. With reference to SEQ ID NO: 1, exon 1 begins at position 1 and ends at position 243 and exon 2 begins at position 244 and ends at position 1380 (or 1377 excluding the stop codon). Suitably, the polynucleotide is an isolated or recombinant polynucleotide and/or a contiguous coding sequence. Suitably, the polynucleotide is a contiguous coding sequence encoding a polynucleotide having at least about 80%, at least about 85%, at least about 90%, at least about 95%, at least about 98%, or at least about 99% identity to the sequence from position 1 to position 81 of SEQ ID NO. 2 and/or to the sequence from position 82 to position 459 of SEQ ID NO. 2. As will be appreciated, the invention also encompasses polypeptides including conservative amino acid substitutions, and polynucleotides encoding such polypeptides.

As used herein, "polynucleotide" includes reference to a deoxyribonucleotide or ribonucleotide polymer in either single- or double-stranded form. The use of the terms "polynucleotide constructs" or "nucleotide constructs" herein is not intended to limit the present invention to nucleotide constructs comprising DNA. Polynucleotide constructs and oligonucleotides composed of ribonucleotides and combinations of ribonucleotides and deoxyribonucleotides, may also be employed in the methods disclosed herein. The nucleotide constructs, nucleic acids, and nucleotide sequences of the invention additionally encompass all complementary forms of such constructs, molecules, and sequences.

It is envisaged the invention encompasses the production of transgenic plants or plant cells by the introduction into a plant or plant cell of polynucleotides encoding a polypeptide comprising a sequence having at least about 80%, at least about 85%, at least about 90%, at least about 95%, at least about 98%, or at least about 99% identity to SEQ ID NO: 2, to the sequence from position 1 to position 81 of SEQ ID NO. 2, or to the sequence from position 82 to position 459 of SEQ ID NO. 2. Suitably, the polynucleotide is provided as a construct in which a promoter is operably linked to the polynucleotide.

It is envisaged that a plant produced by the introduction of such polynucleotides exhibits altered or modified characteristics. The modified characteristics include, but are not limited to, increased growth, reduced fertility, increased leaf area, increased leaf length, increased leaf width, increased leaf number, increased plant height, increased plant diameter, and increased branch length relative to a control or wild-type plant. For example, plants modified according to the present invention may display altered characteristics wherein the leaf area, leaf length, leaf width, leaf number, plant height, plant diameter, and/or branch length is at least about 20%, at least about 30%, at least about 40%, at least about 50%, or at least about 60% greater than a leaf of a control plant.

Plants modified according to the present invention may suitably show reduced fertility or be sterile. For example, plants may show at least a 10%, at least a 20%, at least a 30%, at least a 40%, at least a 50%, at least a 60%, at least a 60%, at least a 60%, at least a 90%, at least a 95%, at least a 98%, at least a 99% reduction in the number of seeds produced compared with a control plant.

As used herein, a "control plant" is a plant that is substantially equivalent to a test plant or modified plant in all parameters with the exception of the test parameters. For example, when referring to a plant into which a polynucleotide according to the present invention has been introduced, a control plant is an equivalent plant into which no such polynucleotide has been introduced. As used herein, "sterile" means that a plant is unable to reproduce naturally.

The polynucleotides of the present invention may be introduced into a plant cell to produce a transgenic plant. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media.

Suitably, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. Suitably, the polynucleotides may be operably linked to at least one, at least two, at least three, at least four, at least five, or at least ten promoters.

Promoters useful in the practice of the present invention include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

Polynucleotides may also be provided in a vector. Suitable vectors include plasmids and virus-derived vectors. Vectors known in the art that are suitable for transformation into plants, cloning, and protein expression may be used.

It is envisaged that the invention encompasses isolated polypeptides comprising SEQ ID NO: 2, which is the amino acid sequence of the protein product of the poplar SAP, or polypeptides comprising from position 1 to position 81 of SEQ ID NO. 2, and/or from position 82 to position 459 of SEQ ID NO. 2. Suitable SAP polypeptides according to the present invention may have at least about 80%, at least about 85%, at least about 90%, at least about 95%, at least about 98%, or at least about 99% identity with SEQ ID NO: 2, with polypeptides from position 1 to position 81 of SEQ ID NO. 2 and/or from position 82 to position 459 of SEQ ID NO. 2. Polypeptides of the present invention suitably promote division of cells, such as plant cells, and accordingly, the invention provides methods for increasing the rate or amount of cell division in cells and/or maintaining cells in a stage or phase where cell division occurs, for example, in a meristematic stage. Suitably, polypeptides of the invention may be synthesized and contacted with cells.

Accordingly, the invention further provides for methods of increasing the rate of growth and/or rate of cell division in plants, cells or tissue cultures by contacting one or more plant cells with one or more isolated SAP polypeptides, or otherwise effecting an increase in the amount or concentration of the SAP polypeptide in the plant cell, such as by introducing a polynucleotide encoding the SAP polypeptide into the cell. The polynucleotide may be introduced in a vector or construct and may be expressed transiently. Plant cells may also be transformed with polynucleotide sequences encoding polypeptides of the invention, such that the polynucleotide stably integrates into the genome or chromosomes of a plant cell.

The polynucleotides may be introduced into the plant or plant cell, either alone or in combination with other polynucleotides. It is envisaged that the expression of the SAP polynucleotides in plant cells, suitably under the control of an inducible promoter, may assist in regenerating plants transformed with other polynucleotides of interest. For example, the expression of the SAP polypeptides may promote cellular regeneration, and may be particularly useful in transformation of plants which are difficult to culture or to regenerate from culture. Without being limited by any theory, it is believed that the SAP polypeptides of the invention may be involved with or stimulate cell division, may promote cells to divide continuously, and/or may promote the retention of cells in a meristematic phase. The invention further provides plant or plant cells produced by the expression of polypeptides of the present invention exhibits altered phenotypes described above.

A variety of plants are suitable for use with methods, polynucleotides and polypeptides of the present invention. For example, as described in the examples below, both poplar and Arabidopsis plants transformed with the poplar sequence shown in SEQ ID NO: 1 displayed a phenotype evidenced by larger leaves and exhibited increased growth. The transformed Arabidopsis plants also may have reduced fertility as they produced thin siliques, which appeared to be sterile. It is envisaged that the transformed poplar plants will also show reduced fertility or will be sterile.

The plants that can be used in the methods of the invention include any amenable to transformation techniques, including both monocotyledonous and dicotyledonous plants. Suitable plants include, but are not limited to, woody plants and crop plants. Crop plants may include, for example, alfalfa, cotton, maize, rice, tobacco, grapevine, wheat, barley, rye, oat, soybean, lettuce, cabbage, beets, broccoli, cauliflower, squash, potato and tomato. Woody plants may include shrubs, vines, or trees such as aspen, fir, maple, acacia, box elder, horse chestnut, buckthorn, buckeye, mimosa, alder, birch, hornbeam, hickory, chestnut, cedar, red bud, cypress, buck wheat, dogwood, hawthorn, persimmon, olive, eucalyptus, rubber, euonymus, beech, ash, witch-hazel, holly, juniper, myrtle, larch, sweet gum, poplar, oak, magnolia crabapple, redwood, spruce (Norway spruce, dragon spruce, white spruce, black spruce, Colorado blue spruce, red spruce, Himalayan spruce), pine (bristle cone pine, weston white pine, longleaf pine, ponderosa pine, scotch pine, loblolly pine), sycamore, plane, cottonwood, poplar, plum, cherry, laurel, peach, Douglas fir, sumac, willow, elderberry, mountain ash, bladdernut, yew, linden, hemlock, and elm.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, ovules, stems, fruits, leaves, roots originating in transgenic plants or their progeny previously transformed with a DNA molecule of the invention and therefore consisting at least in part of transgenic cells, are also an object of the present invention. As used herein, the term "plant cell" includes, without limitation, protoplasts and cells of seeds, suspension cultures, embryos, meristematic regions, callus tissue, leaves, roots, shoots, gametophytes, sporophytes, pollen, and microspores.

The invention further provides methods of producing a transgenic plant by introducing in to a plant or plant cell the antisense (reverse complement) of SEQ ID NO.1, or a sequence showing at least about 80%, at least about 85%, at least about 90%, at least about 95%, at least about 98%, or at least about 99% identity with the reverse complement of SEQ ID NO. 1. Suitably, a transgenic plant may be regenerated from the transformed plant or plant cell. The antisense sequence is suitably operably linked to a promoter functional in the plant. Suitably, the plant transformed with the antisense sequence shows sterility or reduced fertility, lower growth and/or smaller leaves.

While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following non-limiting examples are purely illustrative.

EXAMPLES

Example 1

Identification of the SAP Sequence

Hybrid poplar clone INRA 717 (P. albaxP. tremula) was transformed with activation tagging vector pSKI074 using Agrobacterium-mediated transformation. Briefly, *Agrobacterium* cells carrying the binary vector (such as pV-LEGT02) were grown in luria broth, collected by centrifugation, resuspended in induction medium (MS salts, vitamins, 10 μM AS, 10 mM galactose, 1.28 mM 2-(N-morpholino)ethanesulfonic acid [MES], pH 5.0), and induced at room temperature. Explants were soaked for 10-20 minutes in the bacterial suspension under 0.6-bar vacuum and shaken (50 rpm) at room temperature. The inoculated explants were co-cultivated in dark for 2-3 days at 19-25° C. in callus induction medium (CIM) (MS salts, 0.5 μM benzyladenine, 0.5 μM zeatin, 5 μM naphthalene acetic acid, 5 μM 2,4-Dichlorophenoxyacetic acid, 0.3% gelling agent [such as Phytagar™ from Gibco BRL], 0.1% gelling agent [such as Phytagel™ from Sigma], 1.28 mM 2-(N-morpholino)ethanesulfonic acid, pH 5.8). Explants were cultured for 10-30 days in the dark on CIM with 500 mg/L cefotaxime and 50 mg/L kanamycin. Shoot regeneration was induced on shoot induction medium (SIM) (MS salts, 10 μM benzyladenine, 10 μM zeatin, 1 μM N-acetylaspartate, 0.3% Phytagar (Gibco BRL), 0.1% Phytagel (Sigma), 1.28 mM 2-(N-morpholino)ethanesulfonic acid, pH 5.8) for several weeks to months, and explants were subcultured every 2-4 weeks. Regenerated shoots were further screened for kanamycin resistance by rooting in medium supplemented with 0.5 μM indole-3-butyric acid and 25 mg/L kanamycin.

Figure 2:
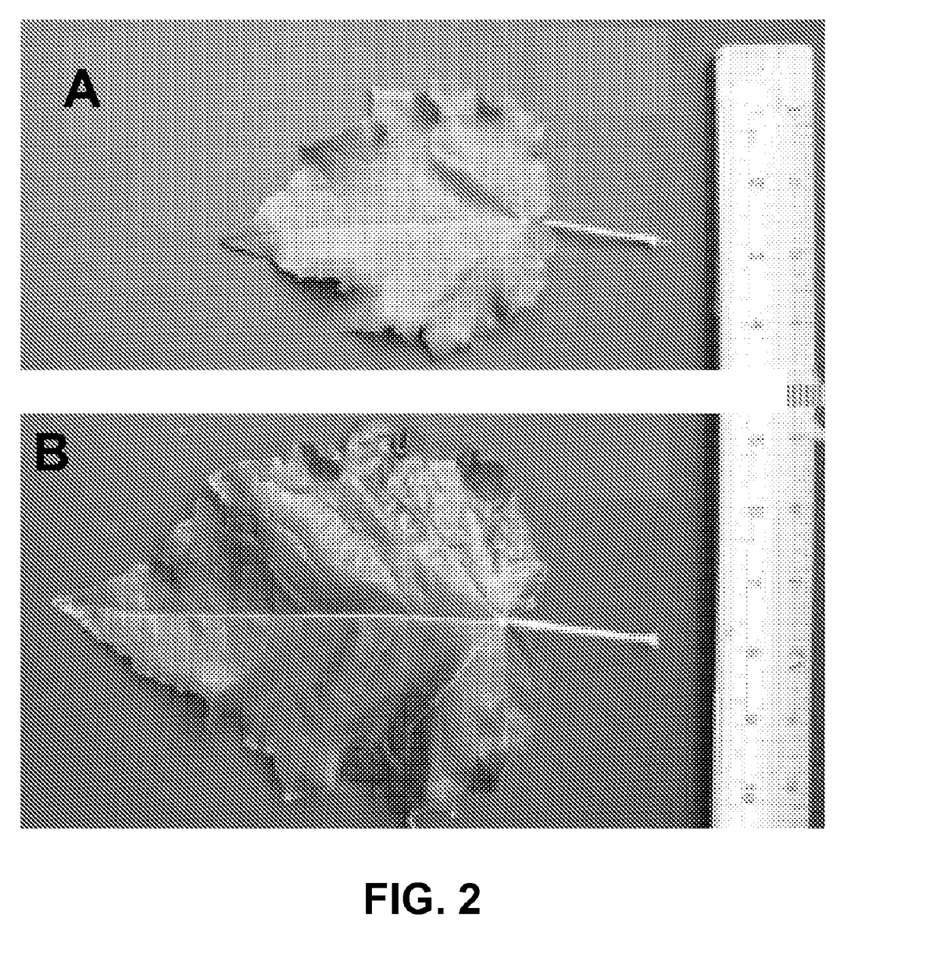
FIG. 2 is a photograph showing a sample leaf from (A) a control poplar plant and (B) a poplar plant over-expressing a SAP polypeptide (SEQ ID NO. 2).

Transgenic lines were recovered after the transformation, and the presence of the activation tagging vector was verified by PCR-amplification using primers specific for the activation tagging vector. Transgenic lines were grown, and in the second year of growth under a field trial, plants displaying big leaves were identified. Leaves were approximately 50% larger than control plants. FIG. 2 shows the difference in size between a leaf from a control plant (WT) and a comparable leaf from a plant overexpressing SEQ ID NO. 2. This big leaf phenotype was consistently displayed in 4 ramets, i.e., clones of the same line.

To identify the DNA sequence responsible for the phenotype, thermal asymmetric interlaced (TAIL)-PCR was used. Briefly, three PCT reactions were carried out sequentially to amplify target sequences using nested primers specific for the activation tagging vector on one side with higher Tm, and a shorter arbitrary degenerate (AD) primer on the other side with lower Tm, so high temperature annealing favored the specific primer. The first reaction included about 5 high stringency cycles, about 1 low stringency cycle, and about 15 super cycles. Each super cycle included 2 high stringency cycles and 1 reduced stringency cycle. The second reaction included about 12 super cycles of 2 high stringency cycles and 1 reduced stringency cycle. The third reaction included about 20 cycles of reduced stringency.

A genomic DNA sequence flanking the left border of the activation tagging vector in the transgenic plants was identified and sequenced. The sequence was used in a BLASTn search of the poplar genome sequence, and the insertion was determined to be located on LG_X at position 9249978. Inspection of the genome regions showed that the vector was inserted in a putative intron sequence of a predicted model fgenesh1_pm.C_LG_XIV000424, consisting of two exons and one intron. RT-PCR was used with primers to amplify the first and second exons as well as the whole cDNA. Primers used to target the exon 1 sequence showed a hyperactivation of this region. In contrast, both full cDNA and exon 2 targeting primers showed down regulation of the whole transcript and the part of the gene downstream of the insertion.

Example 2

Introduction of a Vector Comprising the SAP Sequence into a *Poplar* Hybrid

The coding region of SAP cDNA was PCR-amplified from the transgenic plants. The PCR product was cloned downstream of the CamV35S promoter and upstream of the OCS terminator. The construct was inserted into the NotI site of the pART27 binary vector and transformed into the *Agrobacterium* strain C58 using a freeze thaw method. *Poplar* clone INRA 717 (*P. tremula*×*P. alba*) was transformed using *Agrobacterium*-mediated transformation as described in Example 1. Approximately 40 independent lines were recovered. All transgenic plants were PCR-verified for the presence of the transgene prior to morphological characterization.

Figure 1:
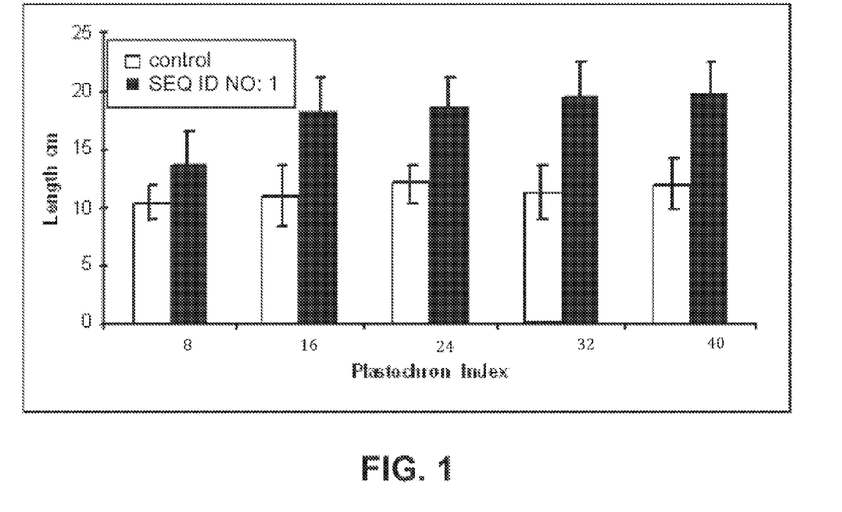
FIG. 1 is a graph showing the correlation of plastocron index and leaf length for control plants and poplar hybrid plants overexpressing the polynucleotides of the invention.

Plants were acclimated to greenhouse environment and grown under standard greenhouse conditions. On average, with a leaf plastochron index (LPI) of 45, transgenic plants displayed 58.5% increase in leaf length relative to control with the increase being most pronounced in the older leaves (FIGS. 1 and 2).

Example 3

Transformation of *Arabidopsis thaliana* With a Vector Comprising the SAP Sequence The vector comprising the SAP sequence of the poplar hybrid (*P. tremula*×*P. alba*), as described in Example 2, was introduced into *Arabidopsis thaliana* using *Agrobacterium*-mediated transformation as described in Example 1. The transformed *Arabidopsis thaliana* displayed leaves that were larger than control *Arabidopsis thaliana*. The transformed *Arabidopsis thaliana* also produced thin siliques and appeared to be sterile.

Example 4

Transformation of *Eucalyptus* and *Pinus* With a Vector Comprising the SAP Sequence The vector comprising the SAP sequence of the poplar hybrid (*P. tremula*×*P. alba*), as described in Example 2, will be transformed into plants from the genus *Eucalyptus* and the genus *Pinus* using *Agrobacterium*-mediated transformation as described in Example 1. It is expected that the transformed plants will display leaves 20-70% larger than control plants and will be sterile or show reduced fertility.

Example 5

In vitro Production of the SAP Protein and Introduction into Plant Cells

The SAP protein from the poplar hybrid (*P. tremula*×*P. alba*), SEQ ID NO: 2, will be expressed in vitro and isolated. Briefly, SEQ ID NO: 1 will be inserted into the multiple cloning site of vector pET21, the vector will be introduced into an *Escherichia coli* expression strain, and the transformed *E. coli* cells will be grown in luria broth and induced to overexpress protein. The *E. coli* cells will be harvested by centrifugation and lysed by sonication. The SAP protein will be further isolated using ion exchange chromatography. Isolated SAP protein will be added to plant cells in culture. It is expected that the SAP protein will promote cellular regeneration.

Example 6

Expression of Antisense SAP Polynucleotide in a *Poplar* Hybrid

The antisense reverse complement of SEQ ID NO: 1 will be inserted into the NotI site of the pART27 binary vector and transformed into the *Agrobacterium* strain C58 using a freeze thaw method. A *Poplar* clone (*P. tremula*×*P. alba*) will be transformed using *Agrobacterium*-mediated transformation as described in Example 1. Multiple independent lines will be recovered, and all transgenic plants will be PCR-verified for the presence of the transgene prior to morphological characterization. Plants will be acclimated to greenhouse environment and grown under standard greenhouse conditions. It is expected that the transgenic plants will be sterile and have smaller leaves than control plants not comprising the antisense sequence.

---

What is claimed is:

1. An isolated polynucleotide comprising: a contiguous coding sequence encoding a polypeptide having at least 95% identity with SEQ ID NO:2, or the complement thereof, or the reverse complement thereof.

2. A vector comprising the polynucleotide of claim 1.

3. A polynucleotide construct comprising a promoter operably linked to the polynucleotide of claim 1.

4. The construct of claim 3, wherein the promoter comprises a constitutive promoter.

5. A plant cell comprising the construct of claim 3.

6. A plant comprising the plant cell of claim 5.

7. The plant of claim 6, wherein the plant exhibits increased expression of the polypeptide, relative to a control plant lacking the construct.

8. The plant of claim 6, wherein the plant exhibits increased growth.

9. The plant of claim 6, wherein the increased growth includes at least one of increased leaf area, increased leaf length, increased leaf width, increased plant height, increased leaf number, increased branch length, and increased stem diameter, relative to a control plant lacking the construct.

10. The plant of claim 6, wherein the plant comprises leaves having an average length at least 20% greater that the average length of leaves of a control plant lacking the construct.

11. The plant of claim 6, wherein the plant has reduced fertility relative to a control plant lacking the construct.

12. The plant of claim 6, wherein the plant is sterile.

13. The plant of claim 6, wherein the plant is a tree.

14. The tree of claim 13, wherein the tree is a poplar, aspen, pine, eucalyptus or sweetgum tree.

15. An isolated polypeptide comprising a sequence having at least 95% identity with SEQ ID NO: 2.

16. A method of producing a transgenic plant comprising:
 (a) introducing into a plant cell a polynucleotide encoding a polypeptide comprising an amino acid sequence having at least 95% identity with SEQ ID. NO 2; and
 (b) regenerating the transformed cell to produce a transgenic plant.

17. The method of claim 16, wherein the polypeptide has activity that promotes cell division.

18. The method of claim 16, wherein the plant exhibits increased growth.

19. The method of claim 16, wherein the plant has reduced fertility relative to a control plant.

20. The method of claim 16, wherein the plant is a tree.

21. The method of claim 20, wherein the tree is a poplar, aspen, pine, eucalyptus or sweetgum tree.

22. A transgenic plant produced by the method of claim 16.

23. A method of producing a transgenic plant comprising:
 (a) introducing into a plant cell a polynucleotide having at least 95% identity to the reverse complement of SEQ ID. NO: 1 and operably linked to a promoter; and
 (b) regenerating the transformed cell to produce a transgenic plant.

24. The method of claim 23, wherein the plant exhibits decreased growth, sterility, or a combination thereof.

* * * * *